United States Patent
Wittmer et al.

(10) Patent No.: US 8,847,602 B2
(45) Date of Patent: Sep. 30, 2014

(54) PLUG-IN MODULE FOR A LIQUID OR GAS SENSOR

(75) Inventors: Detlev Wittmer, Maulbronn (DE); Wolfgang Babel, Weil der Stadt (DE)

(73) Assignee: Endress + Hauser Conducta Gesellschaft für Mess- und Regeltechnik mbH + Co. KG, Gerlingen (DE)

(*) Notice: Subject to any disclaimer, the term of this patent is extended or adjusted under 35 U.S.C. 154(b) by 941 days.

(21) Appl. No.: 11/992,304

(22) PCT Filed: Sep. 20, 2006

(86) PCT No.: PCT/EP2006/066554
§ 371 (c)(1), (2), (4) Date: Jul. 24, 2009

(87) PCT Pub. No.: WO2007/033972
PCT Pub. Date: Mar. 29, 2007

(65) Prior Publication Data
US 2009/0302856 A1    Dec. 10, 2009

(30) Foreign Application Priority Data
Sep. 20, 2005 (DE) .......... 10 2005 044 973

(51) Int. Cl.
G01N 27/416 (2006.01)
G01N 27/28 (2006.01)

(52) U.S. Cl.
CPC ............................. *G01N 27/28* (2013.01)
USPC ......... 324/438; 324/450; 324/600; 324/727; 204/422; 204/424; 73/53.01; 73/64.56; 73/290 R; 73/290 V; 340/603; 340/634

(58) Field of Classification Search
USPC ........................................................ 324/438
See application file for complete search history.

(56) References Cited

U.S. PATENT DOCUMENTS

| | | | | |
|---|---|---|---|---|
| 4,409,980 A | * | 10/1983 | Yano et al. ................ | 600/361 |
| 4,476,706 A | * | 10/1984 | Hadden et al. ............ | 73/1.07 |
| 5,218,304 A | * | 6/1993 | Kinlen et al. .............. | 324/438 |
| 6,182,497 B1 | * | 2/2001 | Krajci ...................... | 73/23.2 |
| 6,252,510 B1 | | 6/2001 | Dungan | |
| 6,396,280 B1 | * | 5/2002 | Nonaka et al. ............ | 324/425 |
| 6,476,520 B1 | * | 11/2002 | Bohm et al. ............... | 307/104 |
| 7,034,660 B2 | * | 4/2006 | Watters et al. ............ | 340/10.41 |
| 8,136,385 B2 | * | 3/2012 | Adams et al. ............. | 73/31.05 |
| 8,519,726 B2 | * | 8/2013 | Sun .......................... | 324/707 |
| 2002/0079902 A1 | * | 6/2002 | Wieland et al. ........... | 324/440 |
| 2004/0232923 A1 | * | 11/2004 | Farruggia et al. ........ | 324/694 |
| 2005/0096513 A1 | | 5/2005 | Ozguz | |
| 2005/0194296 A1 | * | 9/2005 | Lin .......................... | 210/85 |
| 2006/0254911 A1 | * | 11/2006 | Lindmueller et al. .... | 204/424 |
| 2007/0107498 A1 | * | 5/2007 | Thotadakumbri et al. | 73/53.01 |
| 2008/0012579 A1 | * | 1/2008 | Kuhns et al. ............. | 324/652 |

FOREIGN PATENT DOCUMENTS

| | | |
|---|---|---|
| DE | 41 39 121 C1 | 6/1993 |
| DE | 298 01 083 U1 | 5/1998 |
| DE | 197 22 744 A1 | 12/1998 |
| DE | 100 55 090 A1 | 5/2002 |
| DE | 102 55 741 A1 | 6/2004 |
| DE | 103 44 262 A1 | 4/2005 |
| EP | 544237 A1 * | 6/1993 |
| EP | 1 418 243 A2 | 5/2004 |
| EP | 1418243 A2 * | 5/2004 |
| TD | 2 047 786 | 4/1972 |
| WO | WO 2004/086030 A1 | 10/2004 |
| WO | WO 2004086030 A1 * | 10/2004 |

* cited by examiner

*Primary Examiner* — Huy Q Phan
*Assistant Examiner* — Temilade S Rhodes-Vivour
(74) *Attorney, Agent, or Firm* — Bacon & Thomas, PLLC

(57) ABSTRACT

A plug-in module for a liquid- or gas-sensor comprised of a sensor module (SM) and a sensor module head (SMH), which can be releasably connected together, and which, when connected, enable data and energy transfer via a galvanically decoupled transfer section, wherein the sensor module head (SMH) includes an energy supply unit for operating the sensor module head (SMH) and the sensor module (SM), as well as a data memory (MEM), in order to store sensor data received from the sensor module (SM).

22 Claims, 1 Drawing Sheet

PLUG-IN MODULE FOR A LIQUID OR GAS SENSOR

TECHNICAL FIELD

The present invention relates to a plug-in module for a liquid or gas sensor

BACKGROUND DISCUSSION

Liquid- or gas-sensors are used for measuring pH-value or redox potential, temperature, conductivity, or turbidity in liquids.

In the following, the discussion will essentially concern potentiometric sensors, as an example for a liquid- or gas-sensor.

Potentiometric sensors are mostly used for determining potentials in the case of high resistances, such as is the case with pH-measurements and redox measurements. With the help of pH-electrodes, or redox electrodes, the potentials of the solutions are registered.

In many applications, these electrodes are exposed to heavy wear, such that they frequently must be replaced after a short operating time.

There are very simply constructed pH-sensors, which are made up of only one pH-electrode without any other electronic components. These pH-electrodes deliver a pH-dependent potential, which can be tapped at suitable electrical connections. Optionally, for temperature compensation, these pH-electrodes have an integrated temperature sensor, e.g. PT100, the potential of which can be tapped at suitable temperature outputs. For measuring, these pH-sensors are normally connected via a cable to a transmitter, which generates a measurement signal from the pH-dependent potential and, if necessary, from the temperature signal of the temperature sensor.

Besides the simple pH-electrodes, or sensors, described, there are also such with integrated preamplifiers for impedance conversion. The output signal of the preamplifier is the potential of the pH-sensor, with, however, instead of the internal resistance of the pH-sensor, which lies in the order of magnitude of 100 MΩ, the internal resistance of the preamplifier of a few Ω now being determinative. Therefore, the further transfer and processing of the output potential is greatly simplified for a transmitter. The preamplifier is supplied with voltage either via a battery or via a cable.

Furthermore, simple transmitters, which are mounted directly on the pH-sensors, are available under the name "Direct Line" of the firm, Honeywell. These make it possible to generate, right at the sensor, e.g. a 4-20 mA measurement signal, which can then be transferred directly to a control station.

In the case of all known pH-electrodes, or pH-sensors, it is necessary to calibrate the electrodes after connection to the transmitter, in order to be able to store the ascertained calibration parameters in the transmitter. Sensor-specific information, such as the designation of the measuring point, etc., is normally not available on-site, that is, in the direct the vicinity of the sensor.

The sensor system offered by the firm, Endress+Hauser, under the mark, MEMOSENS, includes a sensor module and a sensor module head, which can be plugged together. Data exchange between sensor module and sensor module head, and energy supply to the sensor module, are accomplished inductively via a connecting section, which serves for galvanic decoupling. Furthermore, a sensor module is provided in the digital memory, in which, among other things, calibration parameters are stored. This technology is disclosed, for example, in the German (published applications) DE 100 55 090 and DE 102 18 606.

As an accessory to a sensor as disclosed therein, German Offenlegungsschrift DE 103 44 262 discloses a plug-in module, which especially enables sensor-specific information to be represented on-site, directly at the sensor, and furthermore enables a checking of the measurement values sent to the control station. In a special embodiment, this module is not only suited to display data from the sensor, but also to transfer such to a superordinated unit, per cable or per radio.

In certain applications, data transfer per radio requires an energy expenditure too large to allow sustained operation of the sensor by means of a plug-in module. On the other hand, operation of the sensor by means of a cable, which runs from a measuring transmitter to the sensor, is not always practical, especially in the case of remotely-positioned sensors.

SUMMARY OF THE INVENTION

Therefore, it is an object of the present invention to provide a sensor module head, especially one that can be plugged in, which overcomes the disadvantages of the state of the art.

This object is achieved by the provision of a sensor module head, for a liquid or gas sensor, which includes a sensor module and a sensor module head, which can be releasably connected together, and which, when connected, enable data and energy transfer via a galvanically decoupled transfer section, with the sensor module head having an energy supply unit for operating the sensor module head and the sensor module as well as a data memory, in order to store sensor data received from the sensor module.

In a further development of the invention, the sensor module head can have a display unit, which serves for displaying sensor data stored in the sensor module head.

For further processing or evaluation of the sensor data, the sensor module head can be detached, for example, from the sensor module, and connected to a suitable readout device for reading out the sensor data. The sensor data can include measurement data, whose course was logged over an extended period of time, or the data can concern condition data of the sensor module.

The galvanically decoupled transfer section includes, for example, an inductive transfer section with a primary-side inductive interface in the sensor head module, and a secondary-side inductive interface in the sensor module, with energy supply of the sensor module being accomplished via an AC signal, and wherein data transfer from the sensor module to the sensor head module can be realized by load modulation of the AC signal.

The readout of the sensor module head can be accomplished, for example, via the inductive interface, or an additional interface, provided if necessary.

BRIEF DESCRIPTION OF THE DRAWINGS

The invention will now be described in greater detail on the basis of an example of an embodiment illustrated in the drawing, whose figures show as follows.

DETAILED DISCUSSION IN CONJUNCTION WITH THE DRAWINGS

Figure 1:
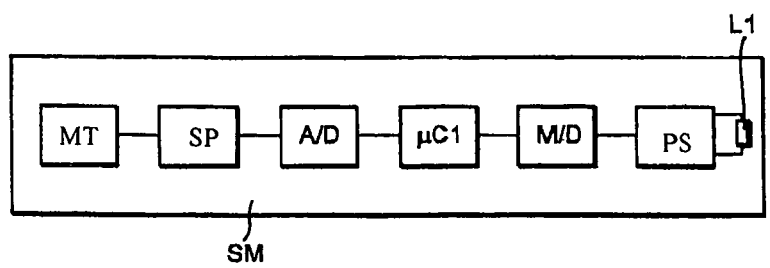
FIG. 1 schematic representation of a sensor module.

FIG. 1 shows a sensor module SM in greater detail. Sensor module SM is composed of a measured value transducer MT (e.g. a glass electrode), which is submerged in the liquid to be measured. The measured value transducer supplies an analog measurement signal, which is pre-processed in an analog signal processing unit SP.

Figure 2:
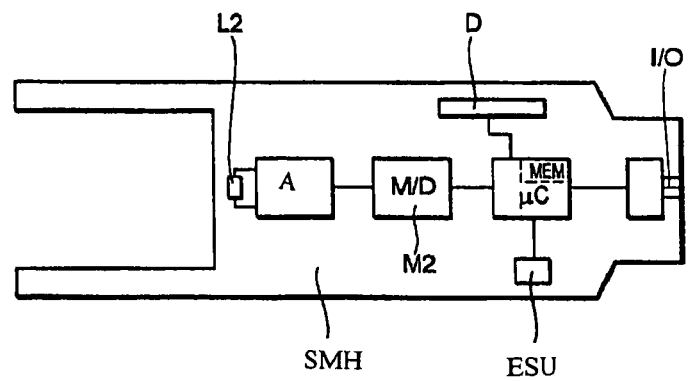
FIG. 2 schematic representation of a sensor module head.

The processed analog measurement signal is then converted in the analog-digital converter A/D into a digital value, which is processed further in a microcontroller μC1. Microcontroller μC1 is connected with a coil L1 via a modem M/D and a power supply PS. The power supply PS provides the entire sensor module with voltage. A sensor module head, shown in greater detail in FIG. 2, is formed such that it fits with the sensor module SM. Thus, the sensor module head SMH and the sensor module SM can be connected together by plugging one into the other. In the sensor module head SMH, a coil L2 is connected with a modem M2 via an amplifier A.

A data and energy exchange takes place via the coils L1 and L2. Further details concerning inductive data exchange via ASK or FSK between the secondary-side sensor module and the primary-side sensor module head, and the energy supply of the sensor module via inductive coupling can be gathered from the above-named German published applications.

Additionally, sensor module head SMH has a microcontroller μC for controlling the components of the sensor module head, with the microcontroller including a data memory MEM, in which sensor data received from the sensor module can be stored. In addition, an energy, or power, supply unit ESU is provided for feeding the components of the sensor module head. The energy supply unit ESU can be a battery or solar cells in combination with an energy storer, for example an accumulator.

Sensor-specific information, such as e.g. measuring point designation, can be represented on an optionally-provided display D. For this, the corresponding data are read out directly from the sensor module SM or from the data memory MEM in the sensor module head.

For reading out the sensor data stored in the data memory MEM, and for programming the microcontroller, a suitable interface I/O is provided.

The application of a supply voltage for charging the ESU can also occur via the interface, for example, or a separate connection can be provided.

The invention claimed is:

1. A plug-in module for a liquid- or gas-sensor, said liquid or gas-sensor comprising:
    a sensor module and a sensor module head being releasably connected together;
    said sensor module comprising a measured value transducer supplying a measurement signal;
    said sensor module head comprising an energy supply unit and a data memory
    said sensor module head and said sensor module, when connected, enable data and energy exchange via a galvanically decoupled transfer section, wherein:
    said energy supply unit operates the sensor module head and said sensor module, as well as said data memory, in order to store sensor data received from said sensor module.

2. The plug-in module as claimed in claim 1, wherein:
    said sensor module head includes a display unit, which serves for displaying stored sensor data.

3. The plug-in module as claimed in claim 1, wherein:
    for further processing or evaluation of sensor data, said sensor module head is detachable from said sensor module and is connectable, by means of an interface, to a suitable read-out device for read-out of sensor data.

4. The module as claimed in claim 3, wherein:
    the sensor data comprise condition data of said sensor module and/or measurement data, whose course was logged over an extended period of time.

5. The module as claimed in claim 1, wherein:
    said energy supply unit comprising a battery or solar cells in combination with an energy storer.

6. The module as claimed in claim 5, wherein:
    said energy storer comprising an accumulator.

7. A liquid- or gas-sensor comprising:
    a sensor module and a sensor module head releasably connected together,
    said sensor module and said sensor module head, when connected together, enabling data and energy exchange via a transfer section,
    said sensor module comprising a measured value transducer supplying a measurement signal;
    said sensor module head comprising an energy supply unit and a data memory, wherein:
    said energy supply unit operates the sensor module head and said sensor module, as well as said data memory, in order to store sensor data received from said sensor module.

8. The sensor as claimed in claim 7, wherein:
    said energy supply unit comprising a battery or solar cells in combination with an energy storer.

9. The sensor as claimed in claim 8, wherein:
    said energy storer comprising an accumulator.

10. The sensor as claimed in claim 7, wherein:
    said sensor data comprises measurement data, whose course is logged over an extended period of time or and/or condition data of the sensor module.

11. The sensor as claimed in claim 7, wherein:
    said transfer section is a galvanically decoupled transfer section.

12. The liquid or gas-sensor of claim 7, further comprising:
    an analog signal processing unit, which pre-processes the analog signal supplied by the measured value transducer and an analog-digital converter which converts the pre-processed analog measurement signal into a digital value.

13. The liquid or gas-sensor of claim 12, further comprising:
    a microcontroller for further processing of said digital value.

14. The sensor of claim 7, wherein:
    said measured value transducer comprises a glass electrode.

15. An assembly comprising:
    a sensor module and a sensor module head releasably connected together,
    said sensor module comprising a measured value transducer, which is submerged in a liquid for measurement, said measured value transducer supplying a measurement signal;
    said sensor module and said sensor module head, when connected together, enabling data exchange via a transfer section,
    said sensor module head comprising an energy supply unit and a data memory, wherein:
    said energy supply unit operates said sensor module as well as said data memory, in order to store sensor data received from said sensor module.

16. The assembly of claim 15, wherein:
    said sensor module head comprises a microcontroller for controlling the components of the sensor module head, with the microcontroller including said data memory, in which sensor data received from the sensor module are stored.

17. The assembly of claim 16, wherein:
said sensor data comprises measurement data, whose course is logged over an extended period of time or and/or condition data of the sensor module.

18. The assembly of claim 15, wherein:
said transfer section is a galvanically decoupled transfer section.

19. The assembly of claim 18, wherein:
said transfer section is an inductive transfer section with a primary side inductive interface in the sensor head module, and a secondary-side inductive interface in the sensor module, with energy supply of the sensor module being accomplished via an AC signal.

20. The assembly of claim 15, further comprising:
an analog signal processing unit, which pre-processes the analog signal supplied by the measured value transducer and an analog-digital converter which converts the pre-processed analog measurement signal into a digital value.

21. The assembly of claim 20, further comprising:
a microcontroller for further processing of said digital value.

22. The assembly of claim 15, wherein:
said measured value transducer comprises a glass electrode.

* * * * *